US Patent Number: 4,477,266
Date of Patent: Oct. 16, 1984
Yang et al.

[54] SOLUTE FOCUSING TECHNIQUE FOR ON-COLUMN INJECTION IN CAPILLARY GAS CHROMATOGRAPHY

[75] Inventors: Frank J. Yang, Danville; John V. Hinshaw, Jr., Martinez, both of Calif.

[73] Assignee: Varian Associates, Inc., Palo Alto, Calif.

[21] Appl. No.: 532,321

[22] Filed: Sep. 15, 1983

[51] Int. Cl.³ .............................................. B01D 15/08
[52] U.S. Cl. .......................................... 55/67; 55/197
[58] Field of Search ............................ 55/67, 197, 386

[56] References Cited

U.S. PATENT DOCUMENTS 4,269,608 5/1981 Sisti et al. .
4,422,860 12/1983 Feinstein .............................. 55/197

OTHER PUBLICATIONS

Capillary Gas Chromatographic Injection System for Large Sample Volumes-W. Vogt et al. Jrnl. of Chromatography, 186, (1979), 197-205.
Sampling Method in Capillary Column Gas-Liquid Chromatography Allowing Injections of up to 250. Jrn. Chromatography, 174, (1979), 437-439.
On-Column Injection on to Glass Capillary Columns—K. Grob et al., Journal of Chromatography, 151, (1978), 311-320.
Automatic Injection in High-Resolution Gas Chromatography: A Programmed Temperature Vaporizer as a General Purpose Injection System Journal of Chromatography, 217, (1981), 81-90, F. Poy et al.

Primary Examiner—John Adee
Attorney, Agent, or Firm—Stanley Z. Cole; Keiichi Nishimura

[57] ABSTRACT

A solute focusing method is applied to the on-column injection of a liquid sample in gas chromatography so that relatively large sample sizes can be used without causing intolerable column flooding. The injection zone of the column is kept originally at a temperature below the solvent boiling point but the temperature in the adjacent downstream zone is kept higher than the solvent boiling point so that the solvent will evaporate and flow downstream, leaving the solute molecules concentrated within a relatively limited length along the column.

4 Claims, 4 Drawing Figures

SOLUTE FOCUSING TECHNIQUE FOR ON-COLUMN INJECTION IN CAPILLARY GAS CHROMATOGRAPHY

BACKGROUND OF THE INVENTION

This invention relates generally to a method of cold on-column injection of a liquid sample onto a capillary gas chromatography column and more particularly to such a method that can be used with a relatively larger sample size without producing the peak distortion or splitting observed under conventional on-column injection conditions.

The two principal objectives of a sampling technique in capillary gas chromatography are to allow identical composition for sample injected onto the column and sample prior to the injection, and to introduce no or minimum extra column band broadening effects so that the total column resolving power is maintained. The former objective is easily achieved by the on-column injection technique because non-vaporizing ("cold") on-column injection, unlike conventional vaporizing injection techniques (split, splitless or direct), can deliver a sample into a capillary gas chromatography column with little effect on composition. The discriminative, adsorptive and thermal effects commonly observed with vaporizing injectors are largely absent, and excellent quantitative accuracy and precision are obtainable. Thus, on-column injection has been successfully applied to a number of difficult sampling problems. As to the latter of the aforementioned objectives, however, intolerable band boardening has been produced by the injection of a liquid sample into a capillary column due to the dynamic spreading of the liquid sample by the carrier gas over a significant length of the column inlet. As described by K. Grob, Jr. in J. Chromatogr., Vol. 213 (1981) at page 3, an on-column injection of a large sample size can result in chromatographic peak splitting due to the effect of the column being flooded by the liquid sample. This liquid sample flooding not only reduces the total available column resolving power and lifetime but also provides minimal use for qualitative and quantitative chromatographic information. The extent of this flooding along the length of the column depends upon the sample size, the column diameter, the carrier gas flow rate, the solvent physicochemical properties, and the column temperature (which affects the viscosity of the carrier gas and surface tension of the liquid sample). In general, a sample size in the range of 1-2 microliters can typically flood a column length of more than 50 cm. A larger sample size up to 10 microliters can easily flood several meters of the column inlet. Thus, this initial spreading of the liquid sample zone is one of the most serious constraints on the use of the method, resulting not only in a non-reproducible peak profile depending on the distribution of the solute molecules within the flooded sample zone but also an extensive peak broadening which is determined by the initial sample bandwidth.

One of the attempts to reduce the effect of liquid sample flooding described by K. Grob, Jr. et al in J. Chromatogr., Vol. 244 (1982) at page 185 has been by removing the stationary phase on the first few meters of the column to prevent retention trapping of the non-uniformly distributed solute molecules. After injection, the flooded column inlet zone is heated up to vaporize sample molecules to be carried downstream to the column zone where stationary liquid traps solute molecules in a narrow initial sample zone. The technique improves the peak shape over that obtained with a conventional on-column injector. This technique, however, has limited success in practical applications due to the following drawbacks. Firstly, it is difficult in practice to strip stationary phase from a column inlet. In particular, nonpolar phases and chemically bonded phases are not completely removable. The use of an uncoated precolumn may allow satisfactory surface characteristics for the requirement of utilizing the retention gap technique, but the practical difficulties and constraints in column connection techniques have to be taken into consideration. Secondly, the retention gap technique does not solve the fundamental problem of sample size limitation. The amount of sample injected is again limited by the length of the retention gap. A sample size of 3 microliters may require 2-3 meters of retention gap to allow satisfactory peak shape. Thirdly, uncoated bare column walls for the retention gap may produce undesirable adsorption effects. Deactivation of the precolumn may not give satisfactory results due to the possibility of retention of solute molecules on the deactivated phase or phases, defeating the retention gap effect. Fourthly, the technique requires that the column oven temperature be cooled down to below the solvent boiling point before every injection. This could require more time than that required for a chromatographic separation. The speed of analysis is thus constrained by the injection technique.

It is therefore an object of this invention to provide a solute focusing method of introducing a liquid sample into a gas chromatographic column.

It is another object of this invention to provide an on-column injection method in gas chromatography which can yield chromatograms of good quality with relatively large sample sizes without causing intolerable peak shape distortion and, hence, useless chromatographic information.

SUMMARY OF THE INVENTION

The above and other objectives are achieved by applying solute focusing techniques to the on-column injection. The injection zone, or the inlet end of the chromatographic column, is kept at a temperature below the boiling point of the solvent while the adjacent downstream zone is kept at a higher temperature so that the following characteristics for an ideal on-column injection process can be achieved: (1) to allow liquid sample injection; (2) to vaporize and separate solvent from solute molecules quickly after injection; (3) to apply solute focusing technique to minimize initial solute molecular zone spreading; and (4) to allow separately temperature programmed injection and vaporization zones to obtain optimum resolution and speed of analysis.

DETAILED DESCRIPTION OF THE INVENTION

Figure 1:
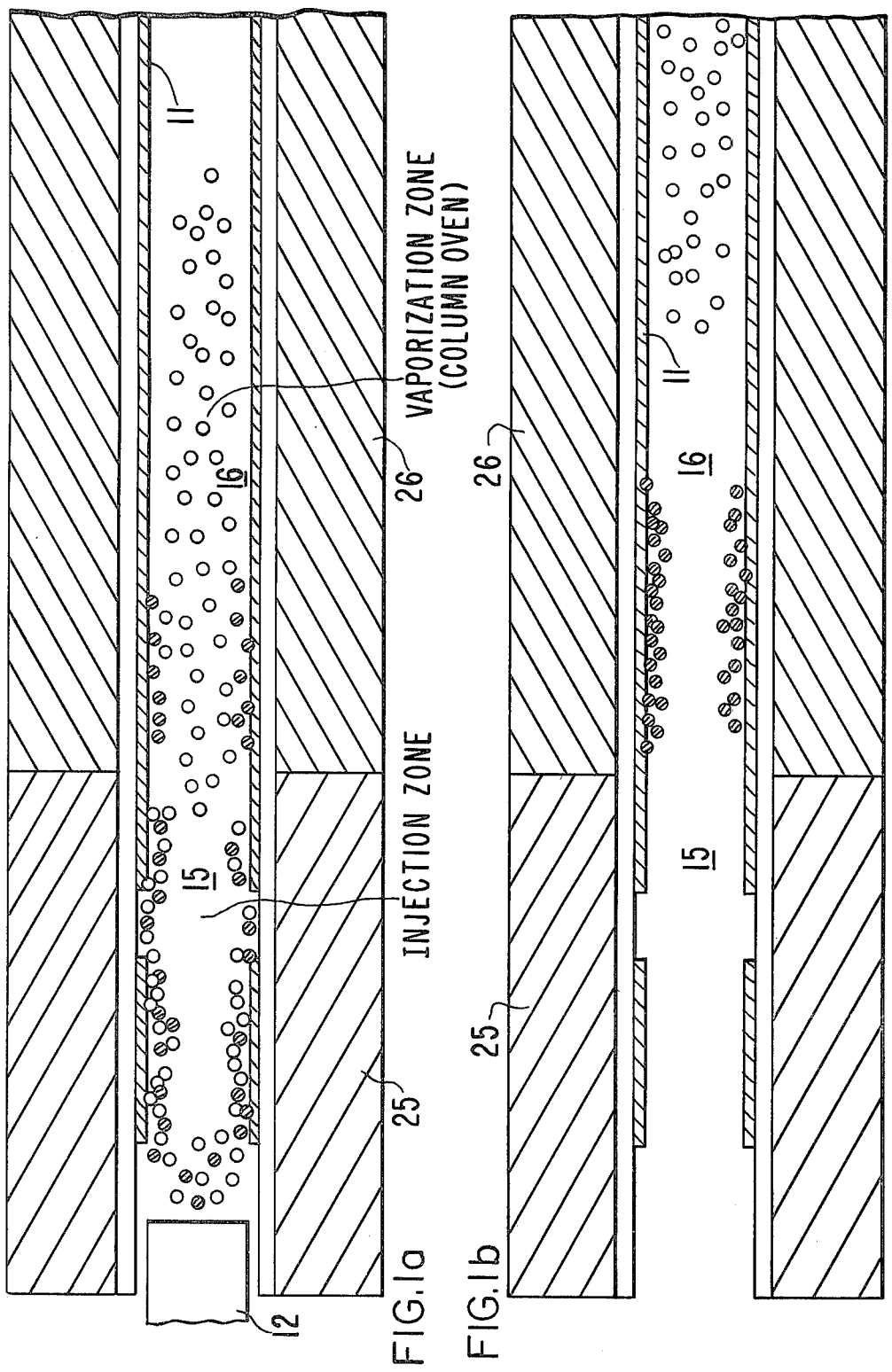
FIGS. 1(*a*) and 1(*b*) show schematically the principle of solute focusing technique which is applied to on-column injection according to the present invention.

The solute focusing technique of the present invention can be practiced, for example, by using the on-column gas chromatographic injector disclosed by P. L. Feinstein in U.S. patent application Ser. No. 342,958, filed Jan. 26, 1982 and assigned to the present assignee. The principle of the method is shown schematically in FIGS. 1(a) and (b). For the sake of simplicity, FIG. 1 illustrates a situation where the liquid sample introduced into a column 11 from a needle 12 consists of only one kind each of solute and solvent molecules (illustrated by shaded and open circles, respectively). An inlet portion 15, to be identified as injection zone, of the column 11 is surrounded by a temperature controlling means 25 including, for example, an electric heater and a cryogenic cooler for regulating the temperature of the injection zone 15. The zone inside the column 11 adjacent to and downstream from the injection zone 15 is identified as the vaporization zone 16 and is surrounded by a second temperature controlling means (column oven) 26 which controls the temperature of the vaporization zone 16. Thus, it is possible to control the injector and oven temperatures independently of each other and to select a variety of different combinations of these temperatures.

In operation, the sample is injected as shown in FIG. 1(a) in its liquid state. For solute focusing, the injection zone 15 is held at a temperature 20° to 40° C. below the solvent boiling point during injection, while the vaporization zone 16 is heated at 10° to 20° C. above the solvent boiling point. During injection, the relatively cold injection zone 15 becomes flooded to some degree with liquid sample. As the liquid is moved downstream by carrier flow and enters the hot vaporization zone 16, the solvent evaporates rapidly, and is carried away by the mobile phase, leaving the solutes trapped in a narrow stationary liquid band at the front of the vaporization zone 16 (FIG. 1(b)). Molecules which may flow back from the vaporization zone 16 will recondense in the injection zone 15 maintained at a low injection zone temperature in the meantime.

Immediately after the introduction of liquid sample is completed, the injection zone temperature is quickly increased to a level significantly higher than the solvent boiling point. This has the effect of driving any residual sample into the vaporization zone 16 where solute molecules are trapped, focused to a very narrow injection sample bandwidth.

After the injection zone 15 reaches this final temperature, normal oven temperature programming is started so that on-column injection can be carried out under the correct non-vaporizing conditions, while flooding of a large column section is avoided. Stripping of the inlet section is not required since band sharpening is achieved by a combination of thermal focusing and retentive focusing (cold trapping). Vapor backflow during injection into the cooled injection zone 15 is not a concern since the entire area is heated after injection.

Figure 2:
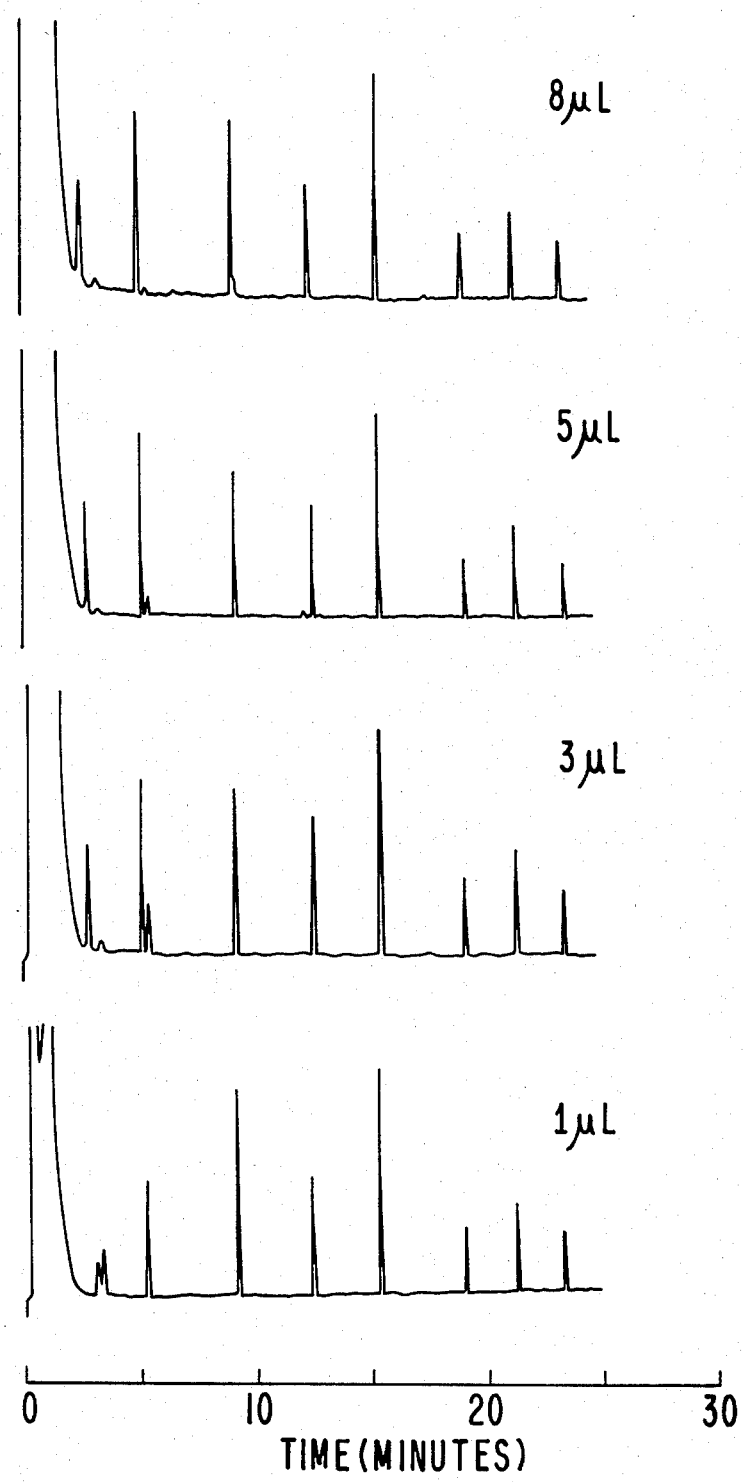
FIG. 2 is a portion of the experimental results according to the method of the present invention, showing the effects of increasing sample size on peak shape.
Figure 3:
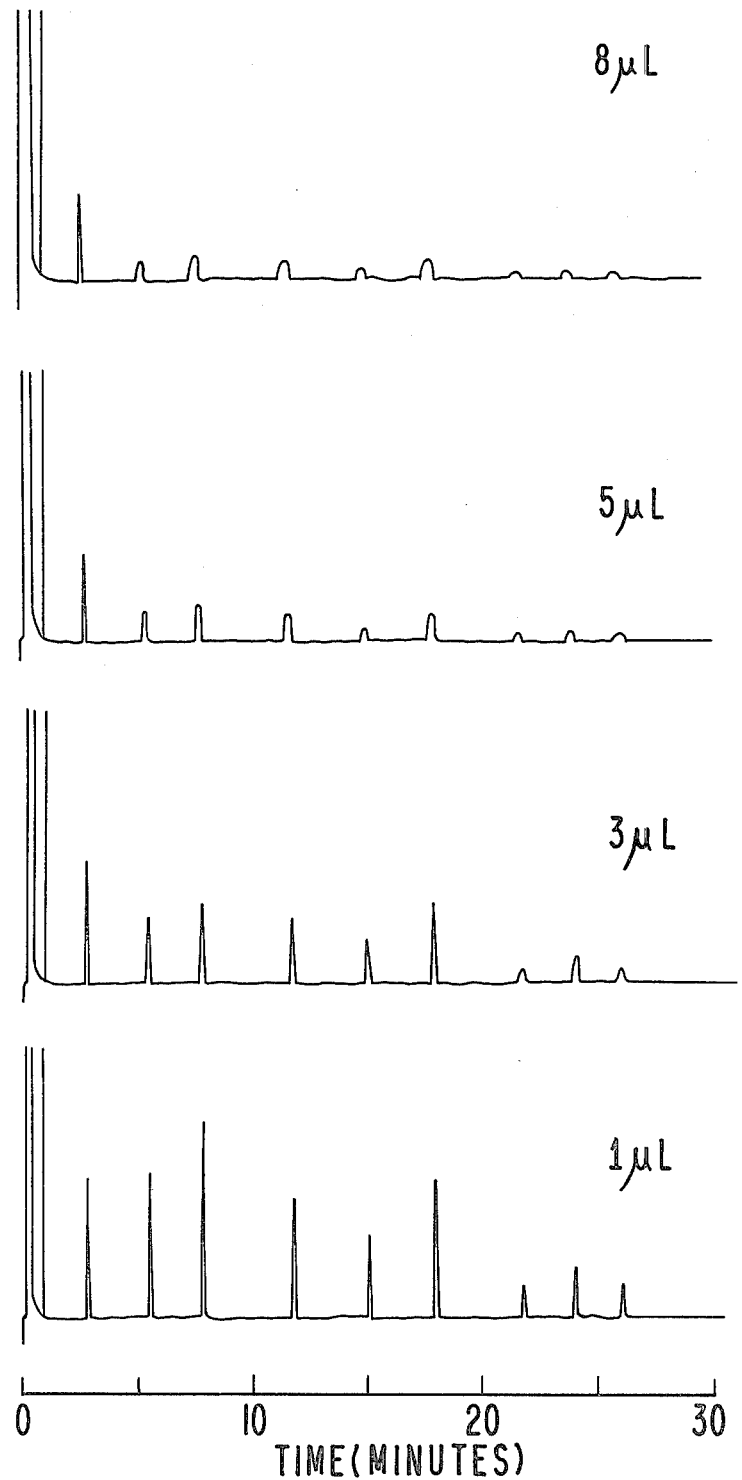
FIG. 3 is a result of comparison experiment without solute focusing, showing the effects of increasing sample size on peak shape.

Experimentally observed effects of increasing sample size on the chromatograph peak shape are shown in Table I below both with and without solute focusing. In these experiments, the sample was an n-alkane mixture in isooctane (boiling at 98° C.). With solute focusing the injection zone temperature was raised from 20° C. to 300° C. at the rate of 180° C./min while the vaporization zone temperature was initially kept at 110° C. for one minute and then raised to 300° C. at the rate of 10° C./min. Without solute focusing, the injection and vaporization zone temperatures were the same and were held for one minute initially at 80° C. and then raised to 300° C. at the rate of 10° C./min. FIG. 2 shows chromatograms obtained with solute focusing under these conditions. In contrast to the results without solute focusing, (FIG. 3), these chromatograms for sample sizes of 1 to 8 microliters show excellent peak shape and nearly constant peak widths from 1- up to 8-microliter injection sizes. Table I lists the experimentally determined peak widths at half height for several peaks from the chromatograms obtained both with and without solute focusing.

TABLE I

| Injected Amount (Microliter) | Solute | With Solute Focusing | Without Solute Focusing |
| --- | --- | --- | --- |
| 1.0 | n-C26 | 3.1 | 3.5 |
|  | n-C30 | 3.0 | 5.5 |
|  | n-C44 | 2.6 | 5.4 |
| 5.0 | n-C26 | 3.2 | 14.4 |
|  | n-C30 | 3.0 | 17.1 |
|  | n-C44 | 3.8 | 18.2 |
| 8.0 | n-C26 | 3.2 | 21.7 |
|  | n-C30 | 3.1 | 22.9 |
|  | n-C44 | 4.0 | 26.7 |

The present invention has been described above only in terms of the general method and one set of experiments. The above description, however, is to be considered as illustrative rather than as limiting, and this invention is accordingly to be broadly construed. For example, FIG. 1 is to be interpreted merely as a schematic illustration so that the depicted dimensional relationships are not intended to be realistic. The length of the injection zone, however, is normally between 10 and 15 cm which can have stationary phase either present or stripped.

The injection and vaporization zone temperatures can also be adjusted conveniently although the vaporization zone temperature should usually be more than 10° C. higher than the solvent boiling point at 1 bar. This initial vaporization zone temperature in a constant flow pneumatics system may be determined by and optimized for the chromatographic resolution and speed of analysis. It can be above solvent boiling point by more than 10° to 15° C. to allow faster analysis time if the solute components of interest can be satisfactorily separated. In a constant pressure pneumatics, however, the applicable initial vaporization zone temperature is limited to about 10° to 15° C. above the solvent boiling point. This is due to the fact that a high vaporization zone temperature could produce rapid vaporization and pressure increase inside the column which could force liquid sample backflow into the injector and result in sample loss and peak shape distortion. A constant pressure pneumatics has also a limited applicable sample size due to the combined gas pressure of the carrier gas, and the vaporized sample inside the column may exceed the pressure at the injection zone during injection process. The proposed solute focusing technique performs best in a constant flow pneumatics system with a gas leak-tight on-column injector. A slow on-column injection of large sample size in a constant flow pneumatics systems prevents backflow of the vaporized sample inside the column because of a constant flow of carrier gas into the column maintained by the constant flow controller. The scope of the invention is defined only by the following claims.

What is claimed is:

1. A solute focusing method of introducing a liquid sample into a gas chromatographic column, said liquid sample comprising solute molecules and a solvent, said method comprising the steps of providing at the inlet end of said column a first temperature controlled zone, providing a second temperature controlled zone in said column substantially adjacent to and downstream from said first temperature controlled zone, injecting said sample into said first temperature controlled zone when the temperature of said first temperature controlled zone is $T_1$, which is below the boiling point ($T_B$) of said solvent, maintaining during said injection step the temperature of said second temperature controlled zone at $T_3$, $T_3$ being higher than $T_B$, and increasing the temperature of said first temperature controlled zone from $T_1$ to $T_2$, $T_2$ being higher than $T_B$, and $T_3$ being higher than $T_2$.

2. The method of claim 1 wherein said temperature increasing step is achieved by a first temperature controller which surrounds said column at said first temperature controlled zone.

3. The method of claim 1 wherein said step of maintaining the temperature of said second temperature controlled zone is achieved by a second temperature controlling means which surrounds said column at said second temperature controlled zone.

4. A solute focusing method of introducing a liquid sample into a gas chromatographic column, said liquid sample comprising solute molecules and a solvent, said method comprising the steps of providing at the inlet end of said column a first temperature controlled zone, providing a second temperature controlled zone in said column substantially adjacent to and downstream from said first temperature controlled zone, injecting said sample into said first temperature controlled zone when the temperature of said first temperature controlled zone is $T_1$, which is below the boiling point ($T_B$) of said solvent, maintaining during said injection step the temperature said second temperature controlled zone at $T_3$, $T_3$-$T_B$ being in the range of 10°–15° C., and increasing the temperature of said first temperature controlled zone from $T_1$ to $T_2$, $T_2$ being higher than $T_B$.

* * * * *